United States Patent
Mullen et al.

(10) Patent No.: US 6,709,739 B1
(45) Date of Patent: Mar. 23, 2004

(54) CLOSED CELL METAL COMPOSITES

(75) Inventors: Robert L. Mullen, Moreland Hills, OH (US); Mehmet Ozgur, Cleveland, OH (US); Gerhard E. Welsch, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 09/980,493

(22) PCT Filed: Jun. 3, 1999

(86) PCT No.: PCT/US99/12303
§ 371 (c)(1),
(2), (4) Date: Jun. 24, 2002

(87) PCT Pub. No.: WO00/74868
PCT Pub. Date: Dec. 14, 2000

(51) Int. Cl.⁷ .............................. B32B 7/04; B32B 15/16; C22C 1/08
(52) U.S. Cl. ................. 428/313.9; 428/317.1; 428/321.5; 428/403; 428/593; 75/230; 75/232; 75/243
(58) Field of Search ............... 428/313.9, 317.1, 428/321.5, 403, 593; 75/230, 232, 243; 419/2, 10, 11, 19, 23, 27, 35, 40

(56) References Cited

U.S. PATENT DOCUMENTS

| | | | |
|---|---|---|---|
| 3,781,170 A | * | 12/1973 | Nakao et al. .................. 75/232 |
| 4,582,534 A | * | 4/1986 | Torobin ......................... 75/229 |
| 4,861,649 A | * | 8/1989 | Browne ......................... 442/372 |
| 4,925,740 A | * | 5/1990 | Norris et al. ................... 428/547 |
| 5,890,268 A | * | 4/1999 | Mullen et al. ............... 29/527.5 |

* cited by examiner

Primary Examiner—Deborah Jones
Assistant Examiner—Jason Savage
(74) Attorney, Agent, or Firm—Fay, Sharpe, Fagan, Minnich & McKee, LLP

(57) ABSTRACT

A plurality of closed metal cells is provided. Each cell encapulates a fluid or a fluid-like filler with a metal skin or cell wall. The closed cells are joined into an aggregate arrangement to form a composite material in which the bonded cell walls form a continuous metal matrix. The cell walls and the encapulated cell filler fluid or fluid-like filler provide controllable stiffness and strength as well as vibration-damping and shock-absorbing characteristics to the material. The resulting closed cell metal composite finds many advantages uses including use as a prosthetic device, a casting, or an automotive component. The component material is elastically compliant or stiff, depending on the design, as well as lightweight and resistant to buckling and crushing. The material provides desirable physical properties such as heat-capacity, thermal and electrical conductivity, vibration-damping capacity, and shock-absorbing characteristics.

18 Claims, 16 Drawing Sheets

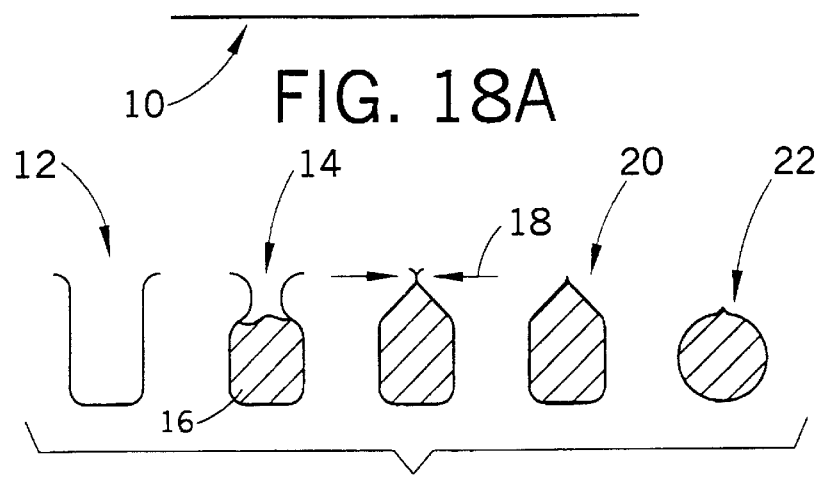
FIG. 18A
FIG. 18B
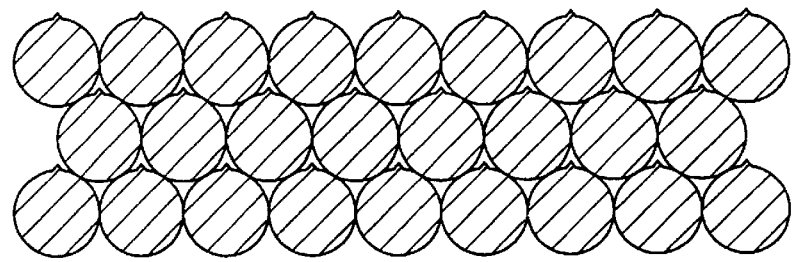
FIG. 18C
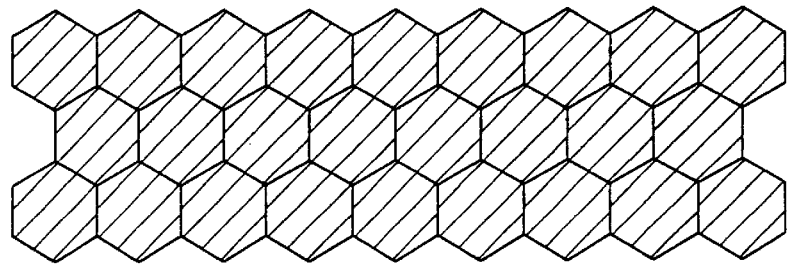
FIG. 18D
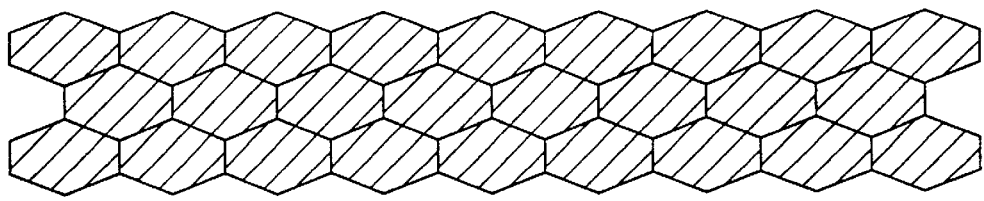
FIG. 18E

CLOSED CELL METAL COMPOSITES

BACKGROUND OF THE INVENTION

Cellular materials can be made to combine high strength to weight ratio, elastic resilience and energy absorbing properties. They are attractive for lightweight structures, packaging and insulating purposes. Nature provides an abundance of examples in wood, leaves, cork, bone and many other organically built structures that display a wealth of intricate and ingenious shapes, forms and designs. Bone and its growth response to stresses is an example of the versatility and of the adaptability of cell structures to mechanical requirements.

Manmade cellular materials have found many applications because it is possible to tailor the properties for a variety of purposes, such as for packaging, insulating, or structural purposes. Open cell structures such as foamed polymers constitute perhaps the most widely used manmade cell materials. Significant developments have also been made in the fabrication of cell materials from metals, glass, ceramics and graphite. Honeycomb structures may be considered as cell structures with designed architecture. They find use in structural applications such as for lightweight aircraft components.

A variety of methods exist for producing cell structures of less well defined design. Such are the foaming methods. Metallic foams are well suited for a variety of applications including impact energy absorbers, silencers, filters, heaters, heat exchangers and structural parts, but more cost effective competitive materials are generally used. Open metal foams were investigated by Ford Motor Company in the early 1970's, but they have not yet found significant use in motor vehicles. One reason for this may be that such foams can be easily crushed in compression due to buckling and plastic collapse of relatively thin cell walls.

The inventors presented their analysis of closed cell metal composites in their published article, M. Ozgur, R. L. Mullen and G. Welsch, "Analysis of Closed Cell Metal Composites" *Acta Mater.,* Vol. 44, No. 5, pp. 2115–2126 (©1996). They also presented the results of finite modelling of pressurized closed all composites in M. Ozgur, R. L. Mullen, G. Welsch, "Finite Element Modelling of Internally Pressurized Closed Cell Composites" *International Journal for Numerical Methods in Engineering,* Vol. 39, pp. 3715–3730 (©1996).

Closed cell metal composites offer advantages over open cell metal foams. An object of this invention is to provide an artificial closed cell metal composite having desirable strength as well as damping or elastic properties. Depending upon the materials used in forming the closed cell metal composites, the resulting bodies can be compatibly adapted for use in a variety of applications ranging from biomedical prostheses to automotive brake disks, various castings and to structural parts.

BRIEF DESCRIPTION OF THE INVENTION

A closed cell metal composite material comprises a plurality of closed structural metal cells that are joined together into an aggregate arrangement. Each cell encapsulates a fluid or fluid-like filler therein in order to provide strength and damping characteristics to the material. Fluid or fluid-like materials may be gases, liquids, powders and solids of relatively low elastic or plastic deformation strength in relation to the cell wall material. The aggregate arrangements of cells serve to provide crush resistance in compression. The cells are at least one nanometer in size. This technology may be utilized in a variety of situations and the selection of the appropriate cell and filler materials coincides with the intended application. Also, it is important to select mutually compatible cell and filler materials.

For example, in the case of biomedical prosthesis, the outer material of the cell walls will necessarily be comprised of a biocompatible material, quite likely titanium or a titanium alloy or gold alloy, stainless steel, cobalt alloy or any metal deemed to be biocompatible. The biomedical cells may encapsulate pressurized gas, or a polymeric material, or a relatively soft metal or alloy of such elements as Li, Na, K, Rb, Cs, Mg, Ca, or a powdered material such as graphite, or a powder or paste or slurry of a substance that is relatively nonreactive and which may have the additional attribute of being biophile. The attribute "relatively soft" is in relation to the elastic and plastic rigidity of the cell wall material. The attribute "relatively nonreactive" is firstly in relation to the metal of the cell wall during processing at low and elevated temperature and during the use lifetime of the cell composite, and it is secondly in relation to the biological environment if the cell composite is used for prosthesis and if the cells' filler substance, either intentionally or unintentionally, can come in contact with the biological environment. The attribute "biophile" relates similarly to biological environment if the filler substance can come into contact with the biological environment. Filler substance can be one or several of the following: stable borides, carbides, nitrides, oxides, and sulfides, also stable fluoride, chloride, bromide and iodide salts, also stable oxynitrides, carbonates, phosphates, sulfates. Examples of boride powder, paste or slurry substances for cell filling are borax and boron nitride; examples of carbide powder, paste or slurry substances for cell filling are silicon carbide and titanium carbide; examples of nitride powder substances for cell filling are silicon nitride and cobalt nitride; examples of oxide powder substances for cell filling are $H_2O$, aluminum oxide, silicon dioxide and titanium oxide, calcium oxide and magnesium oxide; an example of sulfide cell filling is molybdenum disulfide; examples of fluoride, chloride, bromide and iodide salts for cell filling are lithium fluoride, calcium fluoride, sodium chloride, potassium chloride, magnesium bromide, and potassium iodide. The salt fillers may be powders, or liquids, or slurries or relatively soft solids.

Powdered materials such as graphite, calcium oxide, calciumcarbonate, hydroxyapatite bioglass may be encapsulated. When the filler is graphite, carbon will form a titanium carbide layer of a few micrometers thickness along the interior surface wall of the titanium cell wall during elevated temperature processing. This thin film will stop any further reaction of the graphite with the titanium. Calcium and calcium oxide compounds resist being dissolved into the titanium and are therefore stable filler materials during elevated temperature processing. The hydroxyapatite powder is desirable because it offers biocompatibility, as apatite is a main component in human bone. Biocompatibility of the cell filler materials is desired for the event that some of the cell walls in a prosthesis are opened either intentionally or accidentally to the biological environment. The biomedical materials will preferably call for cell structures in which individual cells have sizes ranging from 100 micrometers to roughly a centimeter. The pre-formed closed cells are likely hot-pressed or fusion-bonded together to form the aggregate material from which any number of biomedical items may be formed including hip or joint replacements, rigid fixation devices, pins, nails and dental implants or other prosthetic devices.

When the closed cell materials are intended for use in automotive components such as brake disks, the cells may be comprised of shells made of structural metals that have melting temperatures higher than 500° C., such as steel, and which encapsulate powdered graphite or $MoS_2$. Graphite and $MoS_2$ provide desirable tribological properties to friction brake systems. These cells are joined together in an aggregate body and provide a desirable material for use as a brake disk. Any remaining spaces between the cells of the aggregate may either be left empty or may be filled by liquid infiltration with Al, Mg, Si, casting iron, or a lower melting material than the cells walls.

The closed metal cell composite materials of the present invention are formed by encapsulating a fluid or fluid like filler with a structural metal to provide a filled structural metal closed cell. A plurality of filled structural metal closed cells are then arranged or formed into an aggregate body. The cells are bonded together by sintering, form-pressing, or fusion bonding. A binder may be added to fill the interstices between the cells, if any, and to join the cells together if necessary.

An advantage of the present invention is that the resulting composite material is more lightweight and less dense than the traditional materials they replace. The new composite material provides a way to position a composite blend in an environment without the added weight of traditional materials. For example, disk brakes are traditionally comprised of cast iron, which contains some graphite. Both the iron and the graphite are needed in the operative functioning of the brakes. However, the prior art cast iron is much heavier than the graphite-filled steel closed cells of the present invention.

Another advantage is that when the closed cells comprise titanium and the filler is graphite, these may be aggregated together to form prosthetic devices. The elastic moduli and compliances of the resulting composite are similar to those of bone.

Still other advantages of the invention will become apparent upon a reading of the detailed description herein.

BRIEF DESCRIPTION OF THE DRAWINGS

The invention may take physical form in certain parts and arrangements of parts, a preferred embodiment which will be described in detail in the specification and illustrated in the accompanying drawings which form a part hereof.

FIGS. 18A–E show the steps involved in forming individual cells and then cell aggregates beginning with a steel sheet.

DETAILED DESCRIPTION OF THE INVENTION

The present invention is directed to filled metallic cells comprising walls or shells and filler. The cell-walls are closed and are made of a structural metal or alloy which may include any number of element including tungsten, iron, titanium, copper, as well as Be, Mg, Al, Si, Sc, Ti, V, Cr, Mn, Fe, Co, Ni, Cu, Zn, Y, Zr, Nb, Mo, Tc, Ru, Rh, Pd, Ag, Su, Hf, Ta, Wi, Re, Os, Ir, Pt, An, Pb and the lanthanide and actinide metals, depending on the application. The geometry of the cell wall may vary. For example, some simpler geometries such as those having square, hexagonal or circular cross section may be chosen. Circular cell aggregates will have more empty spaces between contact points than square and hexagonal, and will thus behave differently. Varying sizes and shapes of cells may be distributed within a cell composite. The sizes and shapes may be changed during the processing of the composite.

The properties of the cell structures depend on the material properties of the components, geometrical parameters and on internal cell pressure, as shown for a few examples in Table 1. For purposes of discussion, the properties of the cell wall and cell interior materials are assumed to be isotropic, and only small strain calculations are presented. Variations of the elastic properties are not considered. The cell wall thickness in a given structure is assumed to be uniform. These factors may vary during actual use of the resulting material in its ultimate environment.

TABLE 1

Parameters influencing the properties of cell structures.

| A. Material Parameters | B. Geometrical Parameters | C. Cell Pressure |
|---|---|---|
| Cell Wall: | Cell Shape: | Initial |
| Young's modulus ($E_s$) | Square (face sharing) | Pressure: (Po) |
| Poisson's ratio ($v_s$) | Hexagonal (face sharing) | Compression-Induced |
| Yield strength ($\sigma$) | Circular (point contact) | Pressure: (Pi) |
| Cell Interior: | Cell Length/Width: (h/w) | |
| Bulk Modulus ($\kappa$) | Cell Wall Thickness: ($t_e$) | |

Figure 1:
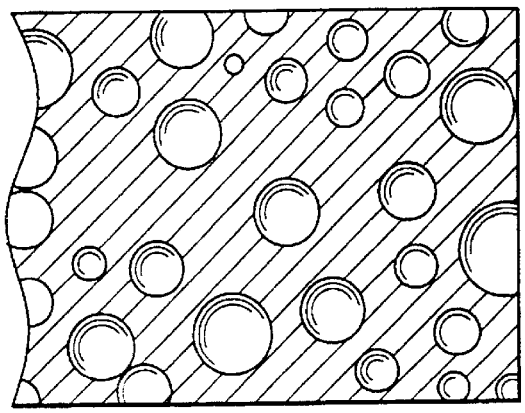
FIG. 1 shows a micrograph of tungsten crystal ion-implanted with potassium and annealed. Potassium bubbles in the solid tungsten range from 500–2000 Å in diameter.
Figure 2:
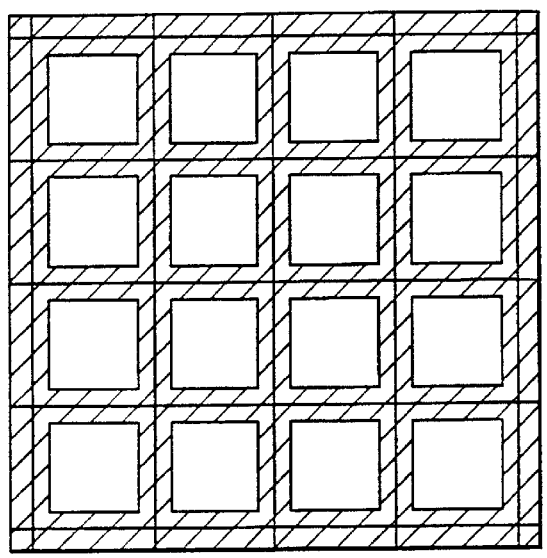
FIGS. 2 and 3 are schematic cross-sections of compression test aggregates of square cells, respectively, wherein the unit "finite element cell" is highlighted.
Figure 3:
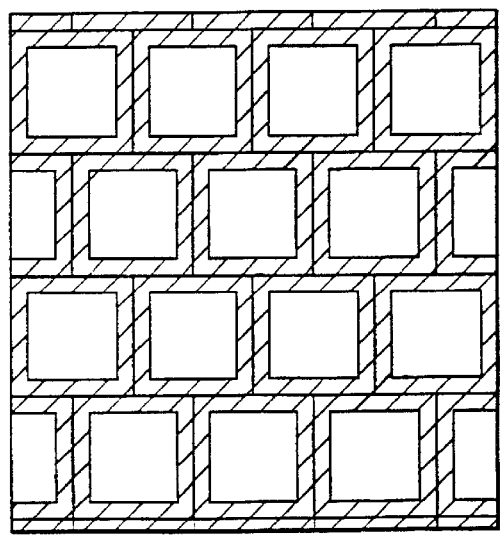
Figure 4:
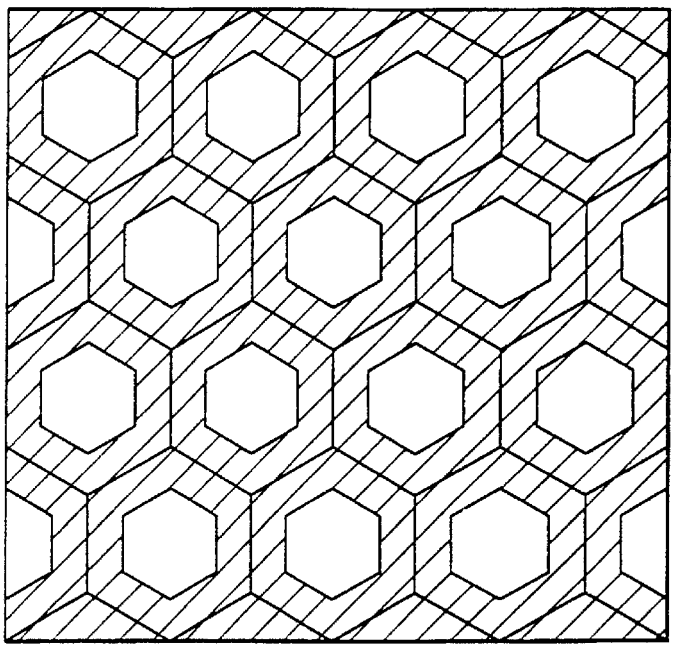
FIG. 4 is a schematic cross-section of a compression test aggregate of hexagonal cells wherein the unit "finite element cell" is highlighted.
Figure 5:
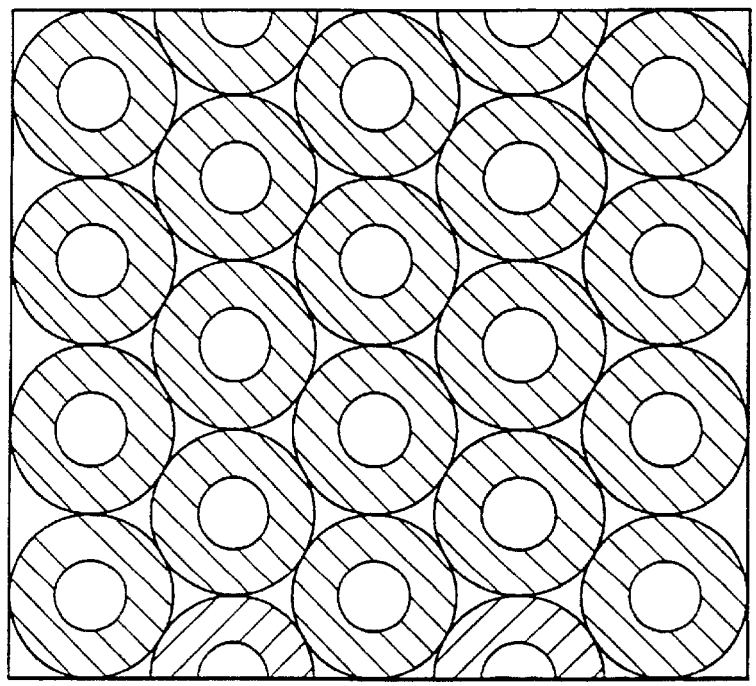
FIG. 5 is a schematic cross-section of a compression test aggregate of circular cells wherein the "structural unit cell" is highlighted.

An actual example of pressurized closed-metal cell structure is that of potassium gas bubbles in tungsten, shown in FIG. 1. In this example the structure was not produced from pre-formed closed metal cells but was instead produced by first ion-implanting potassium into tungsten and then annealing it at high temperature (2300° C.) to form the bubbles. At the annealing temperature the bubble pressures range from 5 to 200 MPa, depending on the bubble size, and are balanced by the surface tension of the tungsten walls. Upon cooling to room temperature the potassium is condensed and forms metallic films on the inside of otherwise void cells. At room temperature it is a cell material with zero internal pressure and at high temperature it is a material of pressurized cells.

More typically, cells are first fabricated individually and in general, the cell-interiors are filled with a fluid, fluid-like solid, i.e, powder, slurry, paste or gas or pressurized gas. The filler is a lightweight and nonreactive filler material which endows the cells with certain physical and mechanical attributes. For example, the fluid filling serves to restrain buckling and hence the collapse of cell aggregates in compression. The cells are aggregated and fabricated into solid bodies by powder metallurgical methods. Interstices between sintered cells may be filled by additional liquid substance in filtration. Depending upon the cell wall and filler materials chosen, the resulting solid bodies are useful in biomedical prosthesis or in various industrial or automotive applications where light weight, damping or elastic resilience capabilities are desired. The cell walls can be comprised of any structural metal. Pure titanium or titanium alloys, for example, are useful in prosthetics, as titanium is biocompatible. The titanium's light weight also makes it useful in aircraft applications. Steel cell walls are used for low cost. Copper-based alloys are easy to form and they provide high electrical and thermal conductives.

The fillers in the cells are lightweight. They are fluid (gas or liquid) or fluid-like (powdered solids). If the material is to be used at high temperatures, consideration is given to the filler's solubility in the cell wall at elevated temperature. For instance, graphite is not soluble in copper and thus graphite particles or powdered graphite is a worthwhile filler for a copper shell. Carbon is slightly soluble in steel. Noble gases are inert and insoluble and therefore make ideal fillers in certain situations. The alkali metals are all insoluble in structural metals and also make good fillers. Polymeric materials and waxes are also acceptable if degradation at high temperatures is not problematic.

In the situation where automotive components are to be made, the resulting bodies are comprised of millimeter to centimeter-sized graphite-filled steel cells. Here, the preferred constituent materials are iron in the form of steel for the cell walls and carbon in the form of graphite or coke for the cell interiors. They are relatively low-cost materials, and the cost per unit volume should not be significantly higher than that of objects made from conventional metallic material, e.g., wrought steel or finished castings.

Bodies made of closed steel/graphite cells derive their properties firstly from the properties of the constituent materials, secondly, from the cell structure and thirdly from the aggregate architecture in the final part. Beneficial physical property gains are found in the parts' light weight, damping capacity, and high thermal and electrical conductivities. Other property advantages are noticeable with respect to elastic/plastic deformability, e.g., resistance to crushing, also with respect to machinability, and tribological behavior. The tribological advantages come from the controlled release of graphite to the contact or wear surface. The desirable properties of graphitic cast iron include machinability, damping capacity and wear resistance. These properties can be greatly extended in a closed cell material whose overall composition (e.g. carbon concentration) is far beyond those allowed by the phase regions in an iron-carbon phase diagram. The drawbacks of cast structures may be avoided or ameliorated by using cell walls that have the microstructure and properties of steel.

There are many potential applications for the closed steel/graphite cells in connection with automotive components. Applications depend on cost, ease of fabrication and the properties of the material. Various final product forms can be envisaged from fabrication methods. These include castings with incorporated cells, sintered cell bodies that are additionally metal infiltrated, powder metallurgical cell bodies, and deformation processed cell components. Potential applications for products made by casting or by sintering plus metal infiltration include the manufacture of engine blocks, cylinder linings, pump housings, brake discs, journal bearings, etc. Powder-metallurgically produced bodies find applications in lightweight panels of frame structures where they are intended to replace honeycomb structures. Densified cell aggregates (impermeable to gas or liquid), e.g., as produced by hot pressing or by sintering plus metal infiltration, are also attractive for gaskets. In a thus fabricated engine block, no additional (cylinder head) gaskets may be required. Densified bodies may also find use in piston rods and crankshafts. Currently, conventionally made steel or cast iron crankshafts contain less than one or less than four weight percent carbon, respectively. Graphitic steel is used for its machinability for ease of drilling oil holes. The cell material of the present invention offers good machinability and the additional advantages of being lightweight and of being damping against mechanical shock and vibration. The cell material of the present invention also has desirable elastic compliance for gaskets at low and at elevated temperatures.

Graphite-filled steel cells may be made by various approaches. For example, when a relatively small number of cells (order of thousand) is desired, they are formed by (a) pinching off and cold-welding segments of steel tubes enclosing graphite powder inside, and (b) encapsulating graphite in stamped or deep-drawn metal capsules. Electrolytically prepared and vapor-deposition-fabricated cells may lend themselves for mass production. In such production methods, the cell wall metal is deposited onto prefabricated pellets or particles of filler material.

The cells may take on relatively simple cell geometries, such as hexagonal, tetrahedral or cuboid (to enable space filling) and spheres or pancake. The cells can be made into a space-filling aggregate by hot pressing and thus deforming the cells from their initial non-space filling shapes. The cell sizes may be in the 0.1 to over 100 mm range, and the volume fractions of cell wall to cell interior will be made to be in the range of 5:1 to 1:100. Their densities will range from 2.1 to 6.8 g/cm$^3$, respectively. In comparison, the density of aluminum is 2.7 g/cm$^3$. Excessive carbon dissolution and cementite formation in the cell walls is to be avoided during elevated temperature processing. One can process below the steel's Al-transformation temperature (727° C.), or a diffusion barrier, such as a thin film of nickel or copper, can be placed at the interface between cell walls and graphite. Incorporation of closed steel/graphite cells into aluminum or magnesium castings should present no problems. When higher processing temperatures are needed, e.g., if the cells are incorporated into an iron casting (i.e., around 1400° C.), it may be useful to use steel walls with reduced carbon solubility in austenite, e.g., by using Si-alloyed steel, noting that the cell wall steel's melting temperature must be greater than the casting temperature of the casting iron, so that the cells remain intact.

As mentioned above, there are various possible approaches for synthesizing cell aggregate bodies that either involve solid state powder metallurgical methods or liquid metal injection into a fixed cell aggregate with open interstices. It is also foreseeable to cast cells mixed into a liquid metal (e.g. aluminum alloy).

Solid state powder metallurgical approaches to synthesizing aggregate bodies include sintering and hot pressing. Sintering of cells occurs in a reducing atmosphere with or without small applied pressure to obtain a non-fully dense material. The aggregation density will depend on the shape of the cells, e.g., cuboidal versus spherical. Hot pressing of cells, preferably in a reducing atmosphere, achieves densification of cell aggregates up to full density.

Methods also exist for synthesizing aggregate cell bodies involving additional infiltration of liquid metal. For example, a cell aggregate assembled in mold will be filled up with liquid aluminum or with liquid magnesium alloy or with liquid C-saturated iron to bond the aggregate. This method may be modified by first pre-sintering the cell aggregate prior to infiltrating with the liquid metal. Here, dense bodies are produced.

Aggregate bodies may be used to make brake disks which traditionally are comprised of cast iron. Cast iron contains up to 20 volume percent graphite. The graphite is needed for the tribological functioning of brake disks. The graphite/steel closed cell structure provides a novel approach to supplying graphite into the brake. The closed cell structure is much lighter in weight than traditional cast iron. Its elastic modulus is lower than that of iron. It maintains its strength by virtue of the steel walls of bonded cells forming a continuous load-bearing matrix and offers higher damping over cast iron. Although cast iron is relatively inexpensive, it is often brittle and heavy. In comparison, the closed cell aggregate structure is lighter and provides an even non-embrittling distribution of graphite. This is particularly important in race car applications.

As for the biomedical applications of this novel closed metal cell technology, the walls of the cells are made of a biocompatible metal, such as titanium or titanium alloy or of any other metal alloy that is deemed biocompatible. The metal cell interiors are filled with a lightweight, low-modulus substance, which preferably is also biocompatible. For example, the metal cells may be filled with graphite, or with sodium chloride or with pressurized innocuous gas. The role of the cell filling is to provide elastic resilience and prevent crushing of thin-walled metal cells in compression.

These structurally designed cell composite materials may serve as the structural material for bone replacement or bone reinforcement in biomedical implants or for prosthesis. Depending upon the cell geometry and on the cell-wall to cell-interior volume ratio, elastic stiffness values may be achieved over the range from less than 1 to over 100 GPa. For bone replacement or bone reinforcement it is desirable that besides having biocompatibility, the stiffness of the prosthesis material be similar to that of the bone with which it forms a union. The prosthesis material should be mechanically similar to that of the bone being replaced. Similarity in elastic deformation enables relatively uniform stress transfer and minimizes regions of stress concentration and stress-shielding which are known to have adverse effects on the regrowth of natural bone and its bonding to the prosthesis.

In biomedical applications, the cell-walls are made of a structural metal, and the cell-interiors are either empty or are filled with lightweight, low-stiffness material. The cell-walls likely consist of titanium alloy. For the cell interiors, graphitic carbon, pressurized (noble) gas, alkali metals (Na, K, Rb, Cs, Ca, Ba, Sr, Li, Be, Mg), and salts of the same alkali metals are potential filler materials. Graphite is an acceptable cell filling because it reacts slowly with titanium due to the formation of a TiC interdiffusion layer. The alkali metals, the noble gases and magnesium and calcium oxide powders are desirable because they resist dissolution into or reaction with the titanium. Elastic stiffness values of bodies constructed from such closed metal cells may range from less than 1 to over 100 GPa. With suitable design they may be made to approach the stiffness of certain bone or other biological tissue. The design takes the following parameters into account:

(1) Cell shape: The metal cells can be made with spheroid, ellipsoid or polygon shapes.

(2) Cell dimensions: Cell sizes can range from ten nanometers to tens of millimeters in diameter, length, and width. The thickness of the cell-walls relative to the overall dimension of the cell can be varied to make the cell composite more or less stiff.

(3) Composite or cell aggregate: Composites may consist of identical cells or may consist of dissimilar cells, i.e., of cells with different shapes and dimensions and of cells with different fillings, depending on the localized mechanical property demands. The cells may be bonded either into "dense" aggregates that are impenetrable to growing tissue or bone, or may be bonded into an "open" composite structure with channels that can be penetrated by growing tissue or bone.

Finite element model calculations have been performed for "dense" material consisting of square and hexagonal cell shapes and for "porous" material consisting of circular cell shapes. For each the cell-wall to cell-interior ratio was varied to show the achievable ranges of stiffness in compression. The results provide guidelines for the design of material with elastic stiffness values similar to that of bone. Stiffness values of human bone have been reported to be in the range of 8 to 25 GPa. To obtain such values with a "dense" square cell composite consisting of closed titanium cell-walls and fillings in the cell interiors, design specifies cell-wall to cell-interior cross-sectional area ratios that are lower for "densified" aggregates of filled cells, and are higher for "nondensified" aggregates.

The prosthesis may be used in a number of internal situations including, but not limited to hip/joint replacements, artificial vertebrae, rigid internal fixation devices, jawbone replacements, and dental implants.

The structural designs may be varied somewhat, depending on the actual cell shapes that can be practically produced. The ranges for cell wall to cell-dimension ratios will be generally valid irrespective of the fabrication aspects. In previous experiments by one of the inventors (Welsch), in which titanium and graphite were combined into a composite with graphite pockets embedded in titanium, it was found that such composite can be subjected to high-temperature (850° C.) pressing without significant adverse titanium-carbide formation. Cross-sectional microstructure analysis showed that most of the graphite was retained in its elemental form, with a thin reaction layer of titanium carbide formed at the titanium/graphite interface. This indicates the feasibility of elevated temperature fabrication of titanium cells with carbon filling and their processing into dense or open composite structures by hot-pressing.

Model Formulation for the Closed Cell Metal Composites

A finite element formulation was developed for two-dimensional elastic-plastic Closed Cell Metal Composites (CCMC). The cell walls were modeled using conventional elastic-plastic linear displacement elements. The Von Mises criterion for yield point of the cell wall material and an isotropic linear strain hardening rule for plastic deformation were used. Some important results of the finite element calculations are stated below.

Elastic Stiffness in Compression

The stiffness and the compressive stress distribution are calculated for the closed cell materials using the two-dimensional Finite Element Method. The cells are assumed to satisfy plane strain condition. Physically, this means that they are long in the direction normal to the plane. Modulus and stresses are calculated from vertically applied compressive displacement using the various geometric arrangements of closed cells, see FIGS. 2–5. Cell types with square, hexagonal and circular cross sections are studied. The subscript "s" indicates a property of the solid cell wall material while a superscript "*" refers to a property of the CCMC.

The effect of the bulk modulus of the internal fluid as well as the effect of cell arrangement is studied for the stiffness of the CCMC. The cell interiors are filled with various fluid-like materials, such as potassium, graphite powder, or magnesium. The bulk moduli, $\kappa$, are normalized relative to the stiffness of the wall material, $E_s (R=\kappa/E_s)$ as shown in Table 2.

TABLE 2

Young's moduli ($E_s$) and Poissons ration ($v_s$) of cell wall materials and normalized bulk moduli ($R = \kappa/E_s$) and absolute bulk moduli (K) of the cell filling materials. (↑ at 923° K., ↑↑ at 336° K.)

| Wall Material | $E_s$ (GPa) | $v_s$ | Interior | $\kappa$(GPa) | $R = \kappa/E_s$ |
|---|---|---|---|---|---|
| Steel ↑ | 155 | 0.3 | Magnesium↑ | 23.81 | 0.1536129 |
| Titanium | 110 | 0.33 | Graphite Powder | 8.33 | 0.0757575 |
| Titanium↑↑ | 108 | 0.33 | Potassium↑↑ | 3.5 | 0.0324074 |
| Titanium | 110 | 0.33 | Inert Gas | 1.0 ×10⁻⁴ | 0.0000009 |

Figure 6:
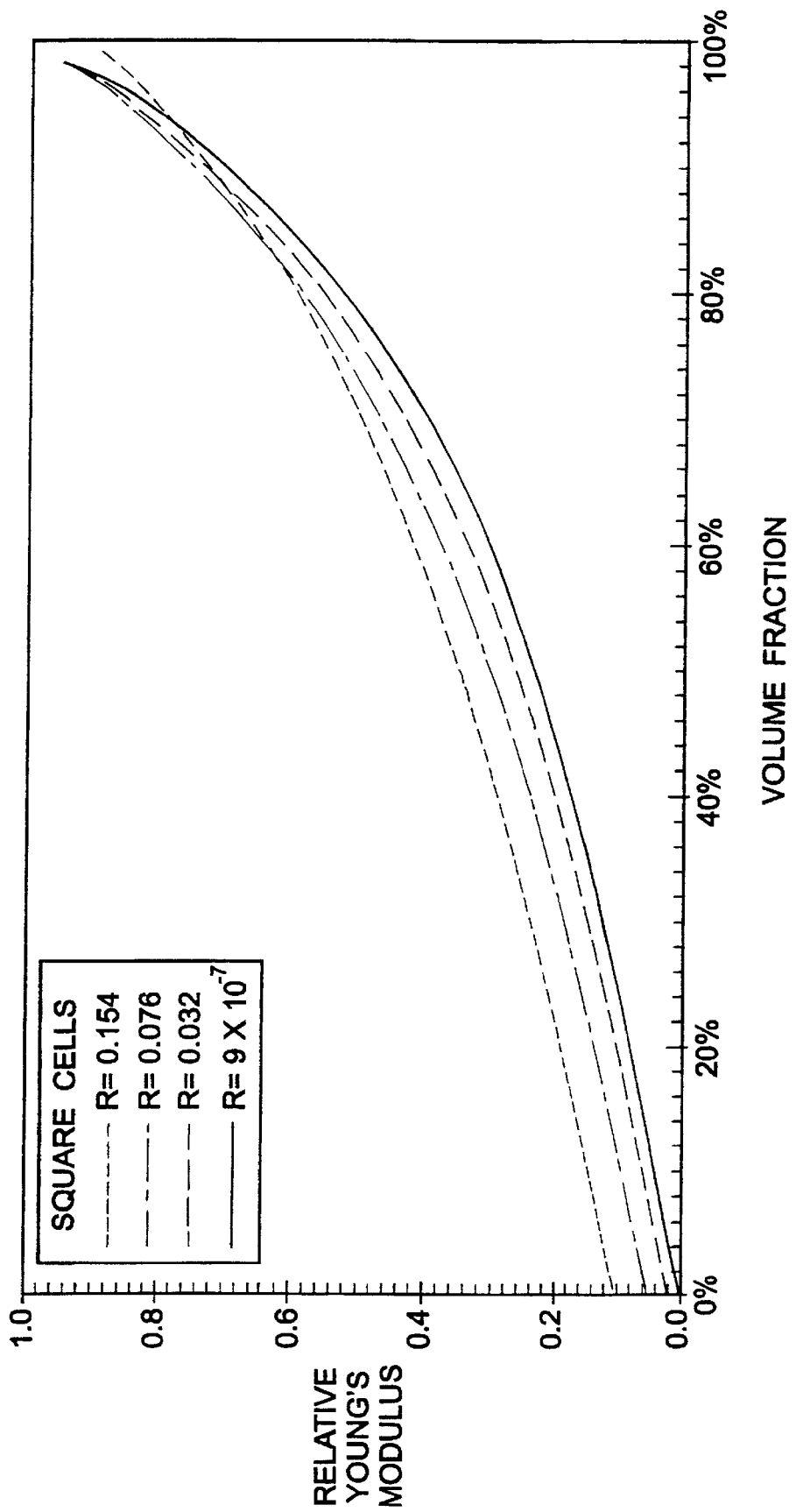
FIGS. 6, 7 and 8 show relative Young's modulus curves for space-filling aggregates of square, hexagonal and circular cells, respectively, each with different cell interiors. Table 2 below shows the materials being represented by their characteristic elastic constants and R values.
Figure 7:
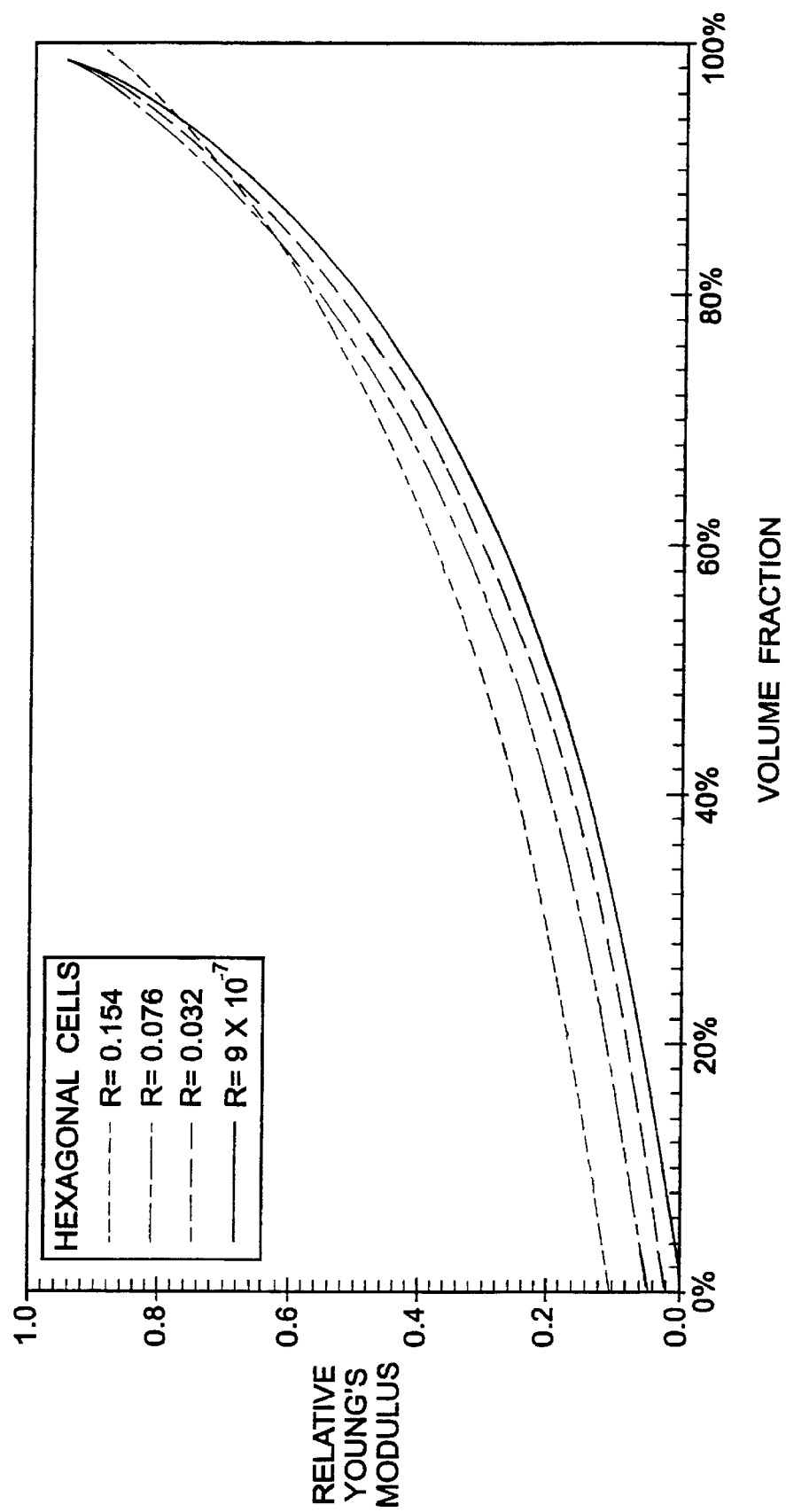
Figure 8:
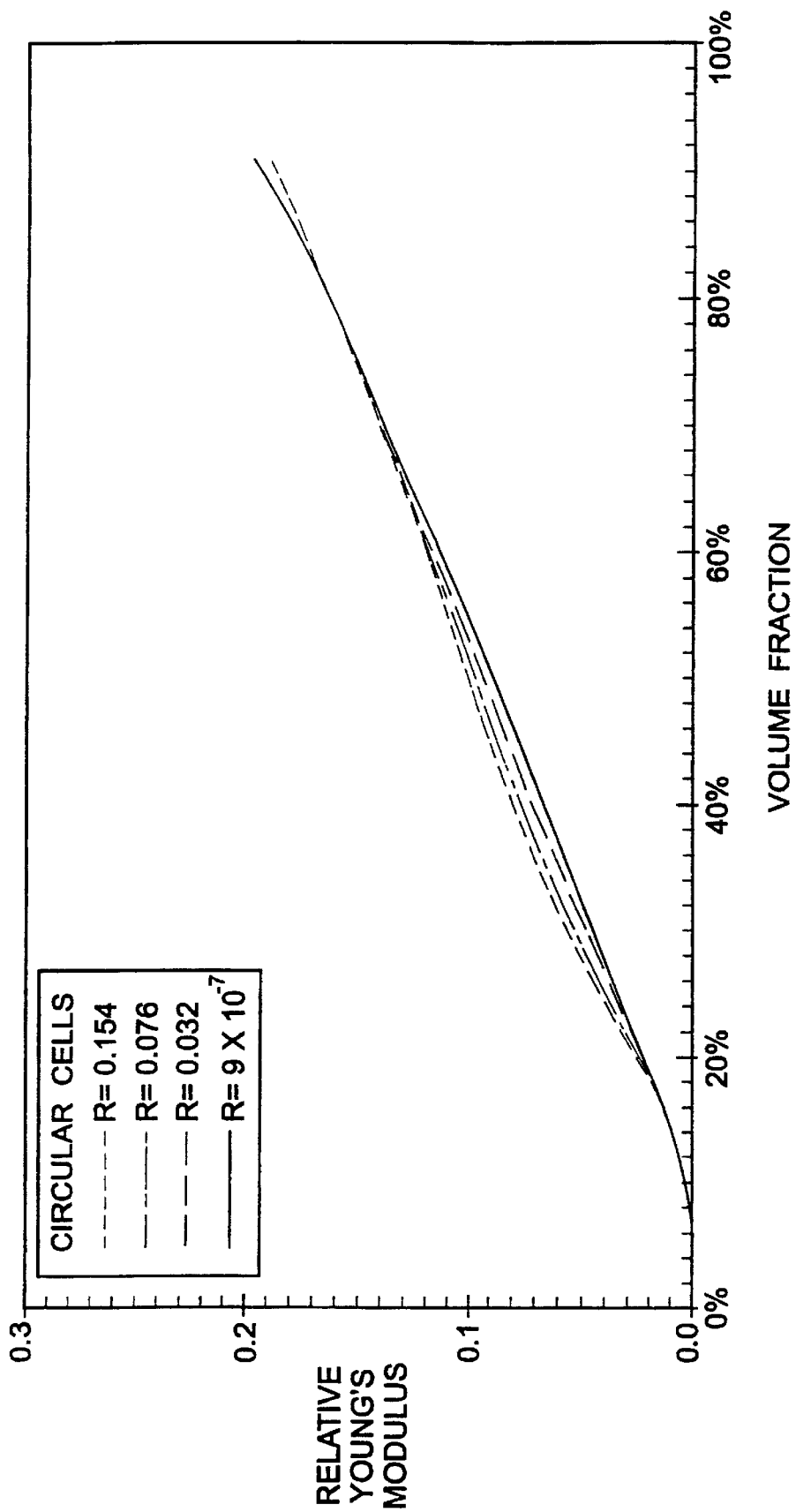

In the stiffness calculations, compressive displacements are applied to the unit cell models having different volume fractions of the solid wall material $f_s=v_s/v^*$. The modulus of the CCMC is calculated from the slope of the elastic stress-strain curve $$E^* = (d\sigma^*_{yy}/d\epsilon^*_{yy})f(v^*)$$

were $v^*$ is Poisson's ratio of the CCMC and $f(v^*)=(1-v^*-2v^{*2})/(1-v^*)$ corrects for unit cell boundary conditions. The composite Poisson's ration, $v^*$, is taken to be 0.33. Compliance curves plotted against volume fractions are given in FIGS. 6, 7, 8 for square, hexagonal and circular cells, respectively. They do not follow rule of mixture predictions. The deviations from rule of mixture properties are especially noticed for intermediate $f_s$ volume fractions and low R values. As volume fraction $f_s$ and bulk modulus of the cell interior $\kappa$ increase, the relative stiffens $E^*/E_s$ increases. When the volume fraction $f_s$ is close to zero, the relative stiffness has the same value as $2R/3$ which is the correct limit when $v^*$ equals ⅓. As volume fraction $f_s$ approaches 1, the stiffness values $E^*$ of the CCMC's approaches that of the cell wall material when $v_s$ equals to $v^*$. However, in steel walled cells, the difference of $v_s$ and $v^*$ result in the lower relative modulus as volume fraction of solid approaches 1. For the non-space-filling aggregates of the circular cells, the stiffness of the CCMC's do not approach that of the cell wall material. It is observed that the relative effects of the cell interior materials are greater when low modulus wall materials are used. The shapes of the cells also have significant effects. Square cells give the highest stiffness results for the particular loading direction considered. One expects anisotropic stiffness when different loading directions are chosen. Circular cell CCMC's have low stiffness compared to the space-filling square and hexagonal cell aggregates. This is due to interstices in the packing and the singular contact point between the cell walls of neighbor cells.

Figure 9:
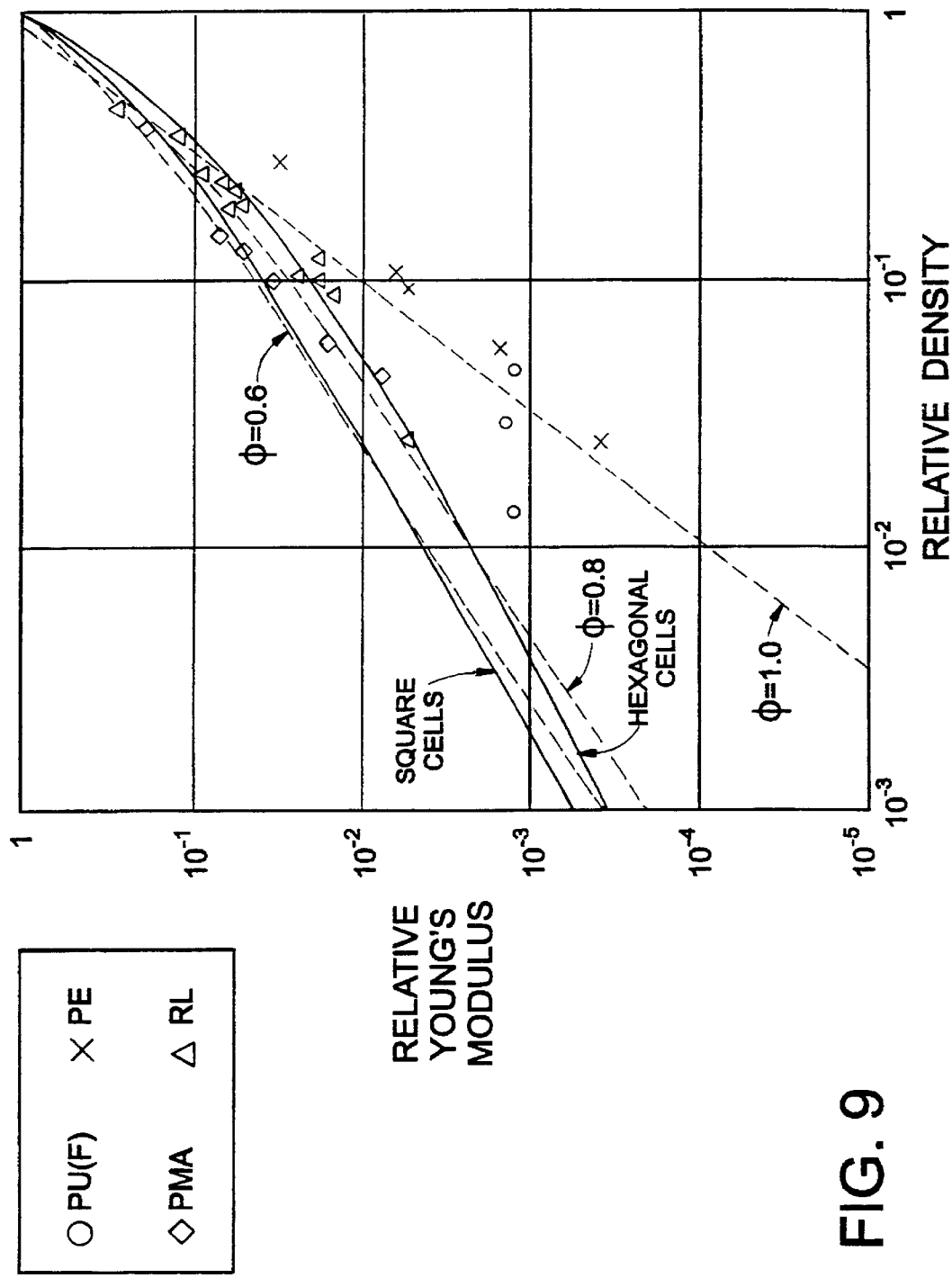
FIG. 9 shows plots of relative Young's modulus, $E^*/E_s$, against relative density, $\rho^*/\rho$, for aggregates made from square and hexagonal shaped cells.
Figure 10:
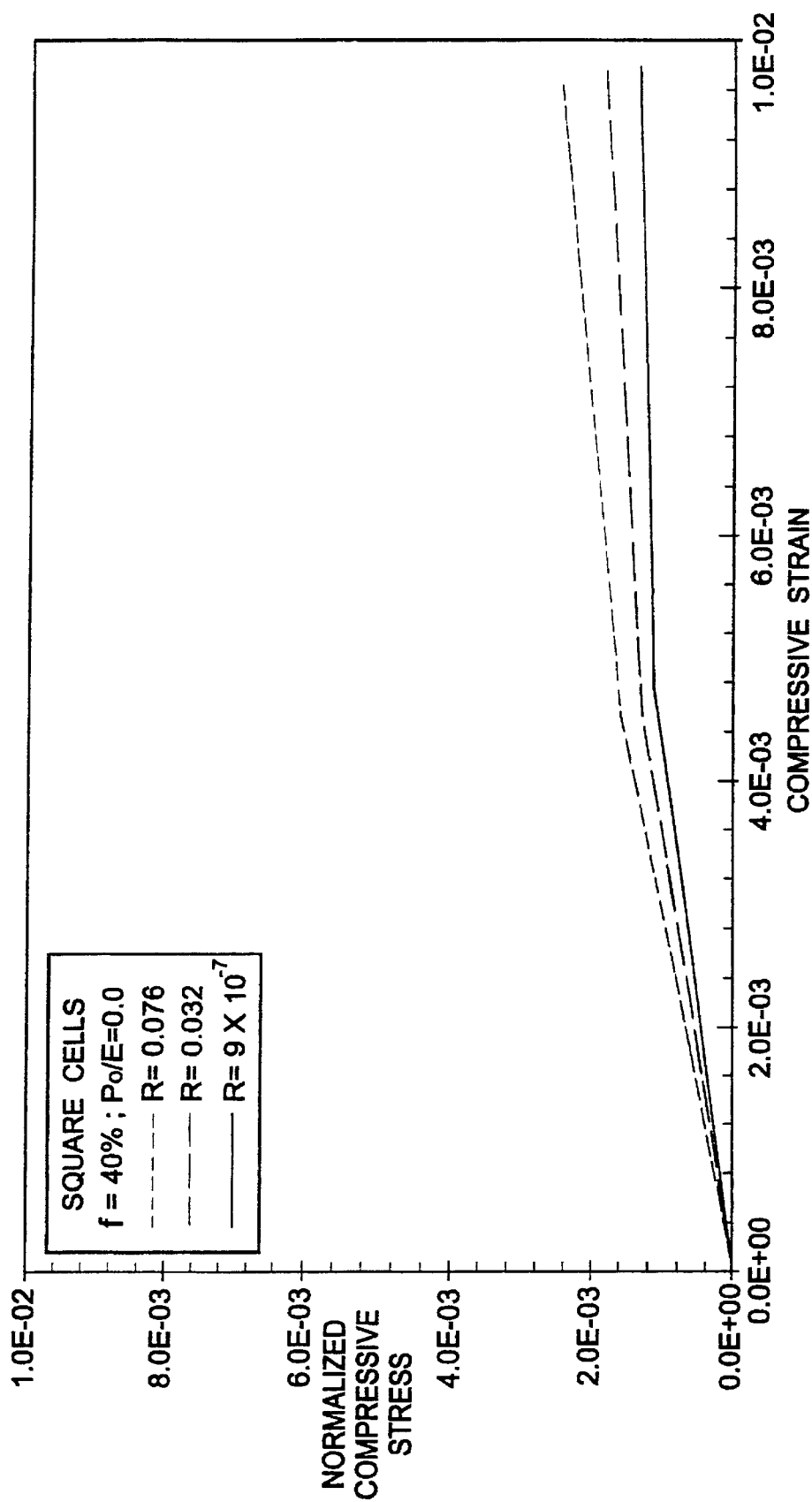
FIGS. 10 and 11 show compressive stress-strain curves for space filling aggregates of square cells for various cell fillings. The materials represented by their elastic constants and R values are shown in Table 2 below.
Figure 11:
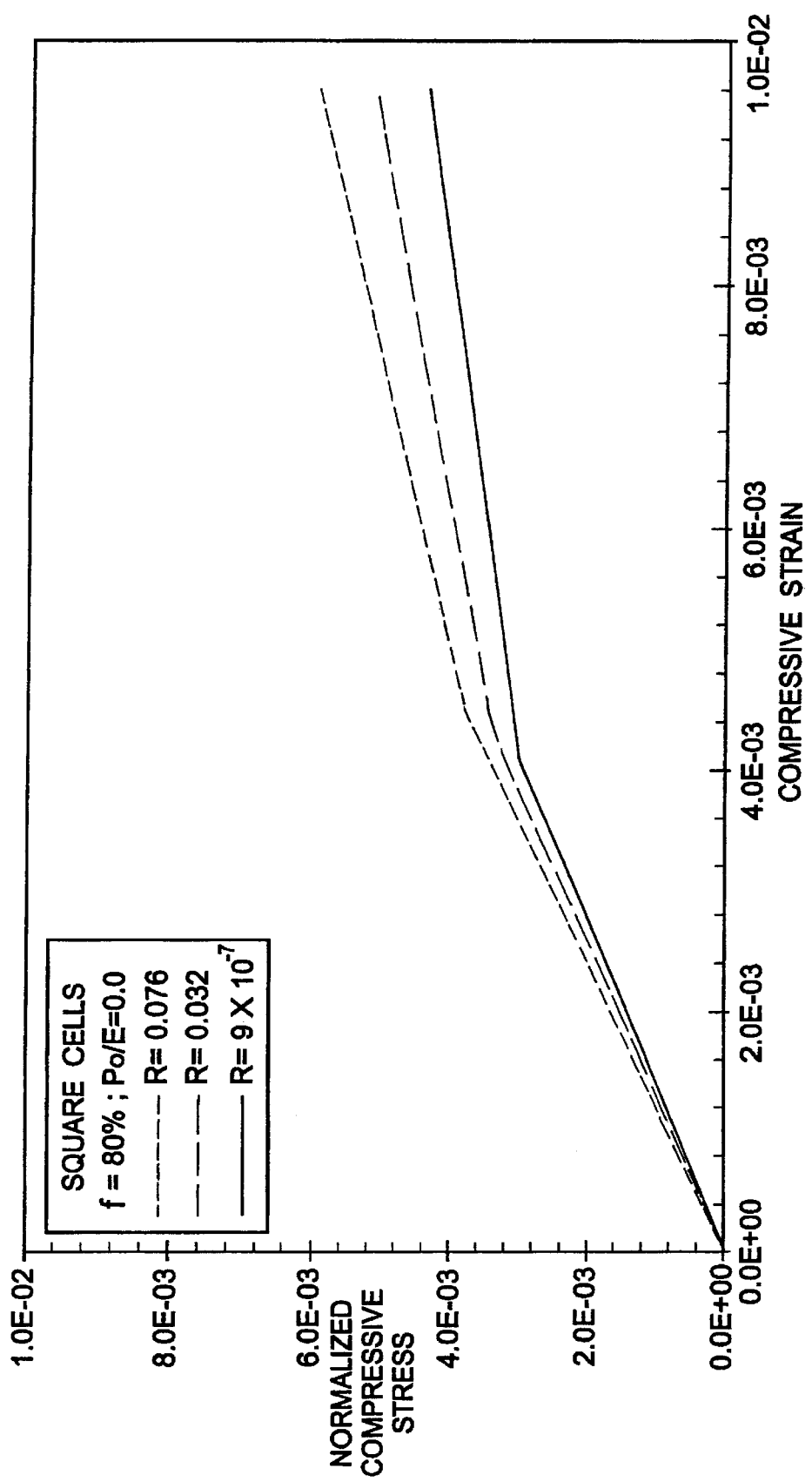
Figure 12:
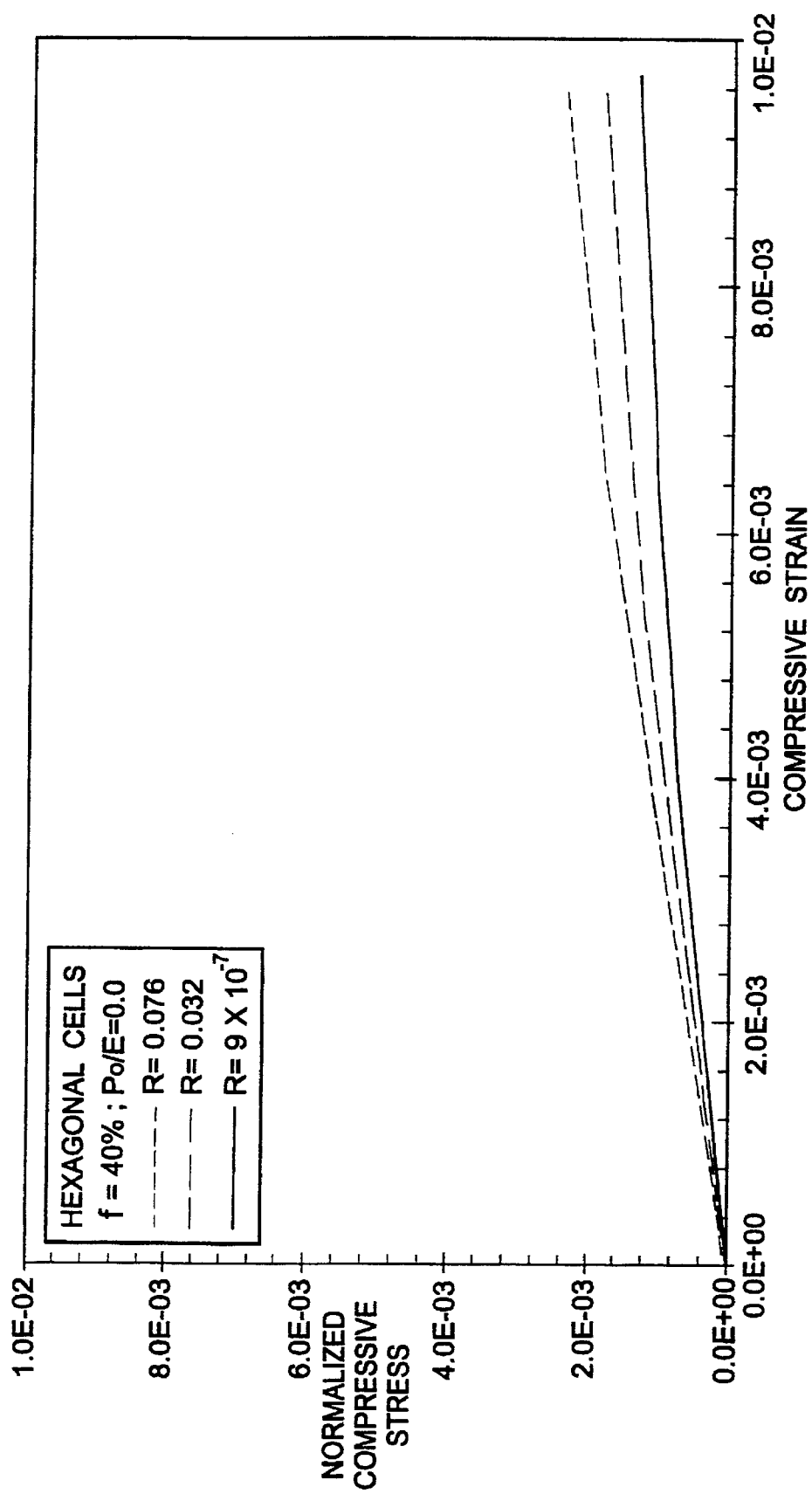
FIGS. 12 and 13 show compressive stress-strain curves for space filling aggregates of hexagonal cells for various cell fillings. The materials represented by their elastic constants and R values are shown in Table 2.
Figure 13:
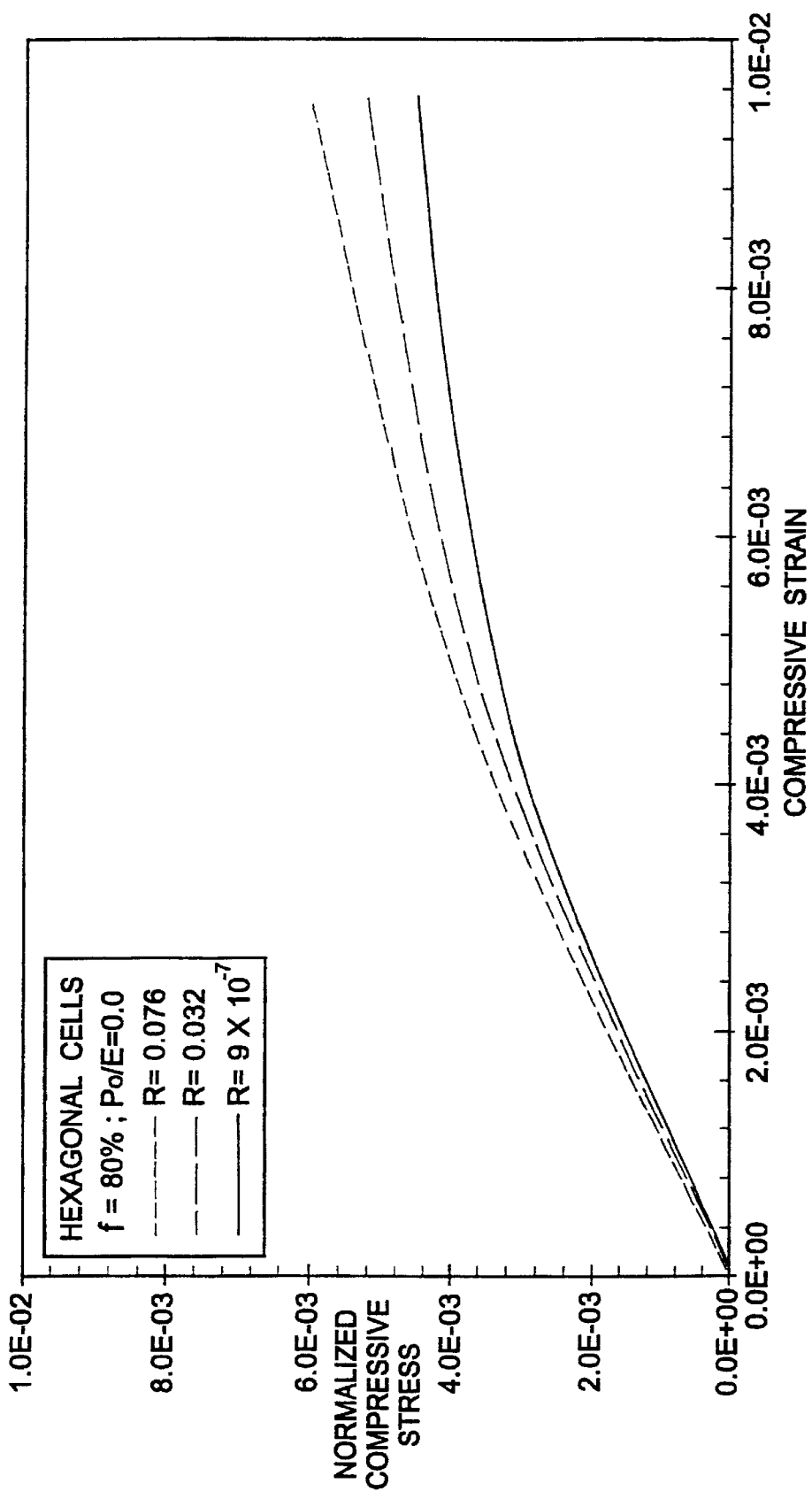
Figure 14:
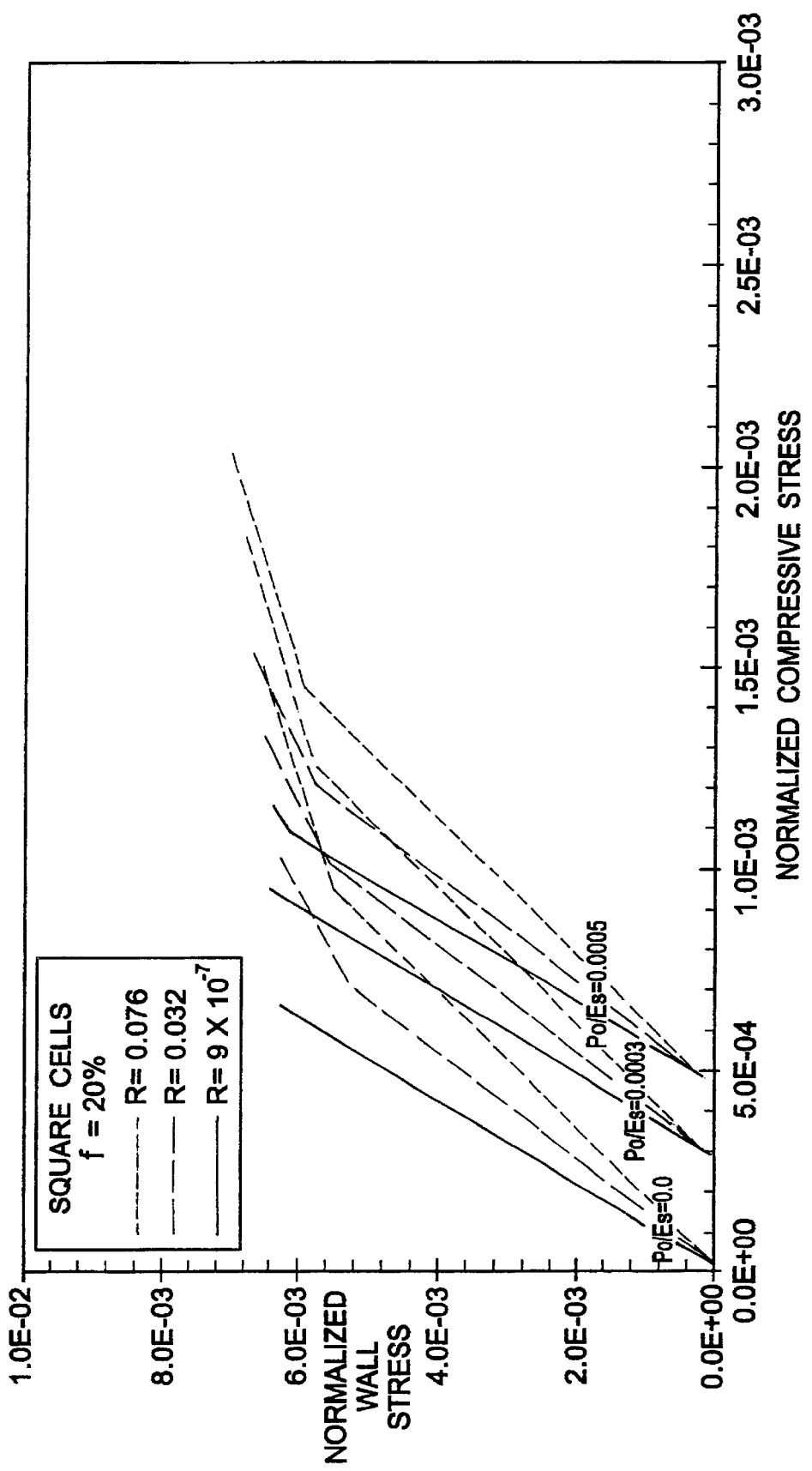
FIGS. 14, 15, 16 and 17 show compressive stress curves for space filling aggregates of square cells and hexagonal cells with different internal pressures.
Figure 15:
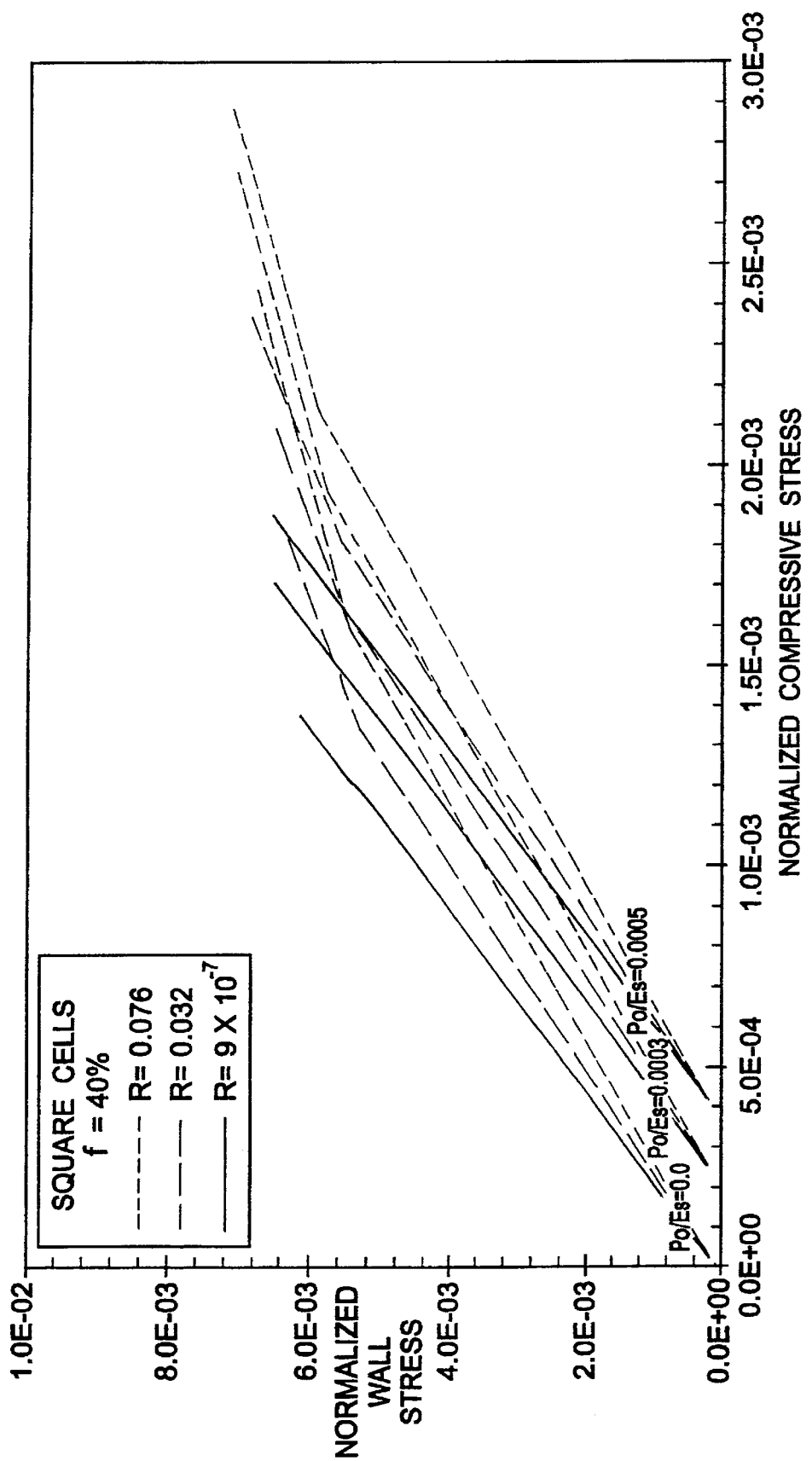
Figure 16:
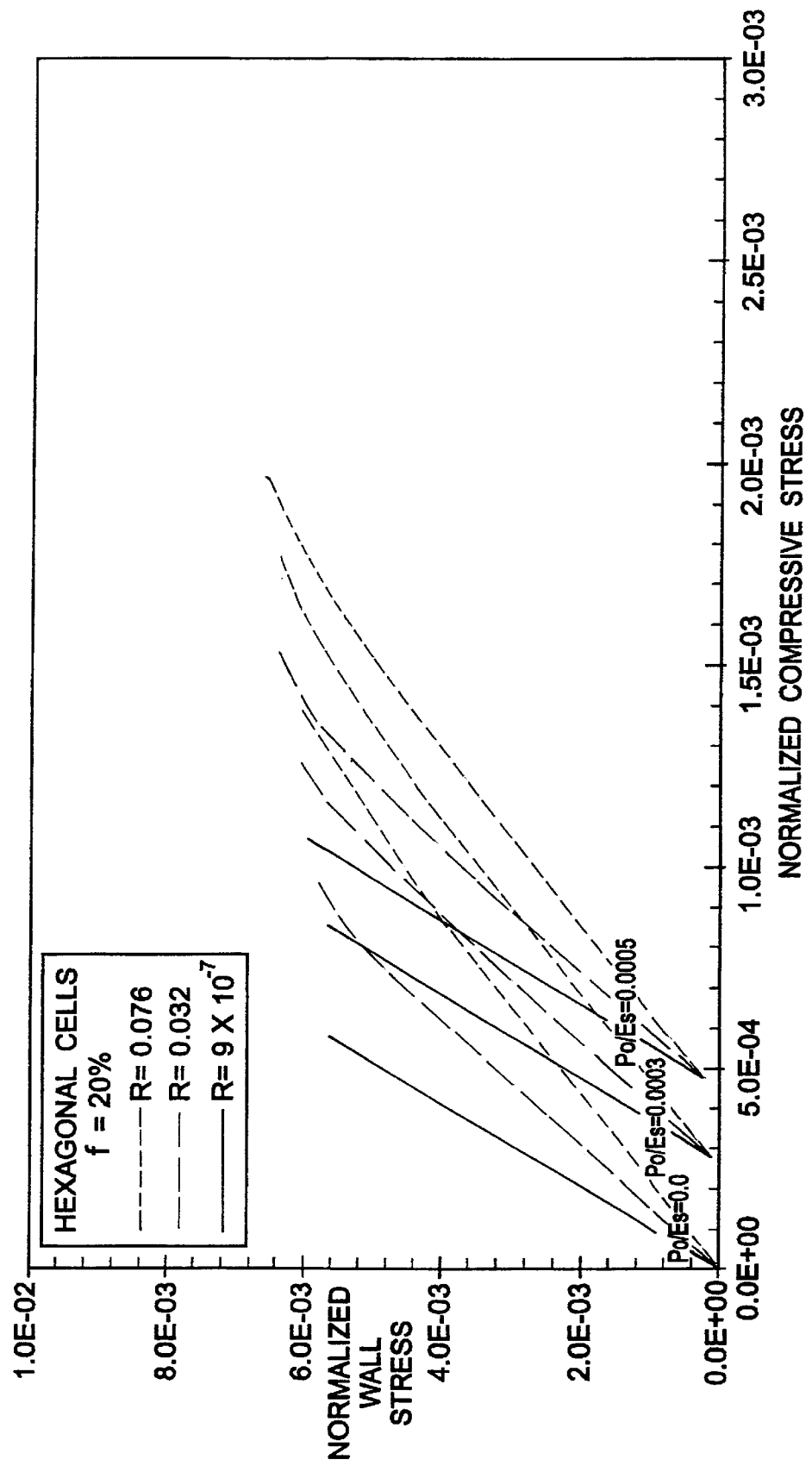
Figure 17:
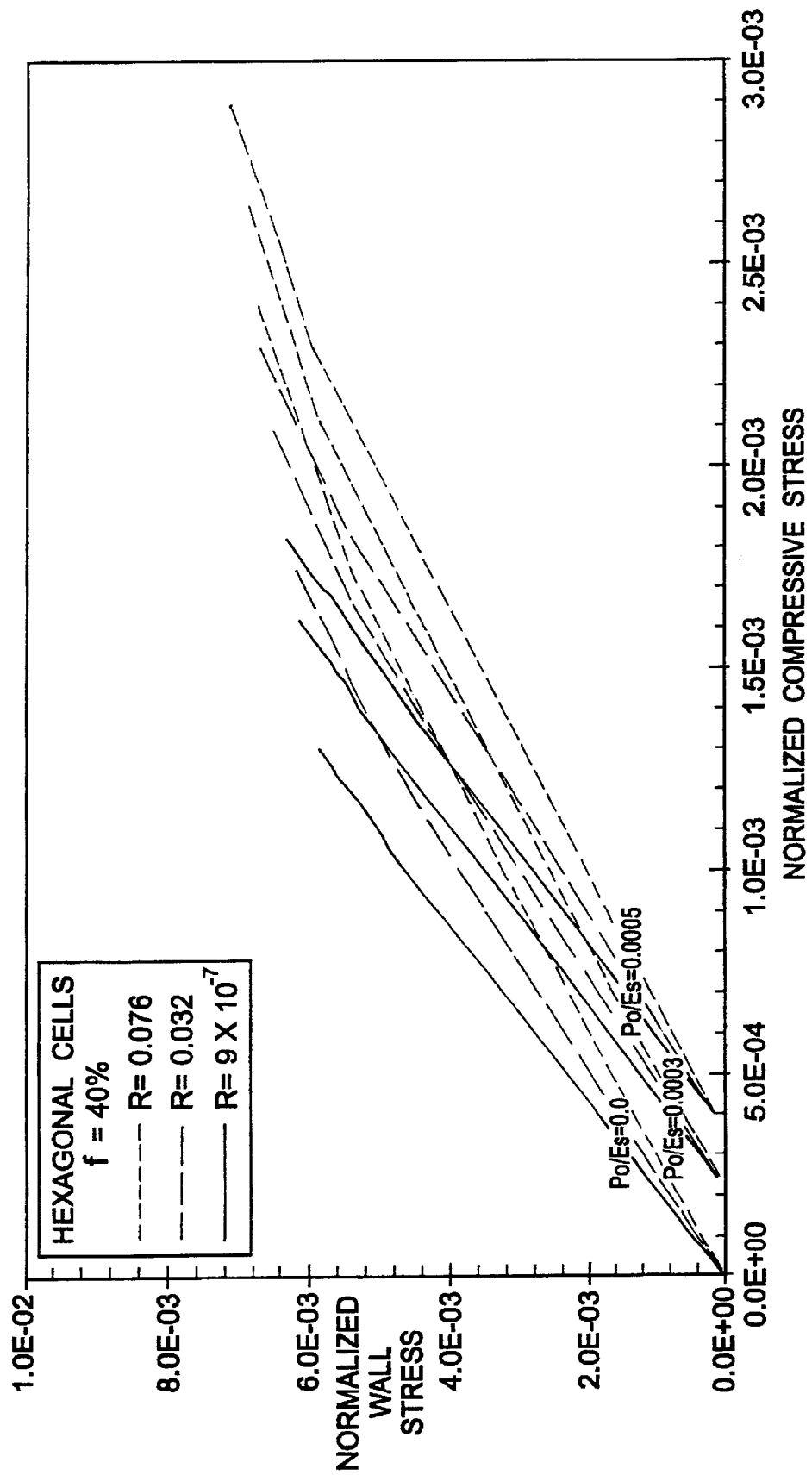

A comparison with experimental data on polymer foams, which have been summarized by Gibson and Ashby in *Cellular Solids, Structure and Properties,* Pergamon Press (©1988), is shown in FIG. 9. The computed relative modulus, $E^*/E_s$ is plotted versus relative density, $\rho/\rho_s$, of space filling, closed cell composites. The dashed lines in the figure are those of Gibson and Ashby's model for cellular materials with $\phi$ being the volume fraction of solid in the cell edges. The structure of polymeric foams for which experimental data are shown in FIG. 9 is mostly of the open cell type, but some structures approach the closed cell geometry of our hexagonal cells. The data for polymethacrylimid, PMA, agree well with our hexagonal cell results.

Elastic-Plastic Deformation

For the study of elastic-plastic deformation of a specific example of CCMC, titanium cell wall material is chosen. The same unit cells and loading, as presented above, are used for elastic-plastic deformation calculations. The cell wall material has a Young's modulus of 110 GPa, a Poisson's ratio of 0.33 and an assumed yield stress of 500 MPa. Beyond the elastic region linear hardening with plastic modulus of 11 GPa is used. The plasticity problem for the CCMC is studied with several internal cell pressures, namely $Po/E_s=0.0$, $Po/E_s=3.0\times10^{-4}$ and $Po/E_s=5.0\times10^{-4}$, where Po is the pressure inside the cells, and $E_s$ is the Young's modulus of the cell wall solid. In the displacement-controlled plasticity problems, strains are incrementally applied from zero to $2\epsilon_p$, where $\epsilon_p$ is the strain for plastic onset in the cell wall material.

The elastic-plastic compressive stress-strain curves for square and hexagonal CCMC's are presented in FIGS. 10 to 13 for cell wall volume fractions of 0.4 and 0.8. As the bulk modulus of the CCMC increases, the yield strength of the CCMC is increased. The hardening modulus of the CCMC also goes up with increasing filler bulk modulus. Plastic deformations of the cell walls result in volume changes of the cell interiors, and in compression higher loads are being carried by the cell interior material. For relatively small volume fractions of cell wall the yield strength is low and the hardening modulus of the composite approaches the Young's modulus of the CCMC. The yield point is well defined in the square cell material when loaded parallel to the cell edges. This is due to uniform loading of the cell walls. In the hexagonal cell material, yielding occurs more gradually due to the bending of the cell walls.

The effect of initial pressure and filler material on the cell wall stresses is shown in FIGS. 14 to 17 as a function of applied traction cell wall volume fractions of 0.2 and 0.4. The wall stress is evaluated at the base element on the left corner of each the square and hexagonal CCMC models. The higher the bulk modulus of the filler, the lower is the wall stress at a given applied traction. Internal pressure provides a tensile bias in the wall stress. The significance of internal pressure is reduced with increasing volume fraction, $f_s$. The onset of plastic deformation occurs more gradually for hexagonal cells than for edge-loaded square cell composites.

Figure 19:
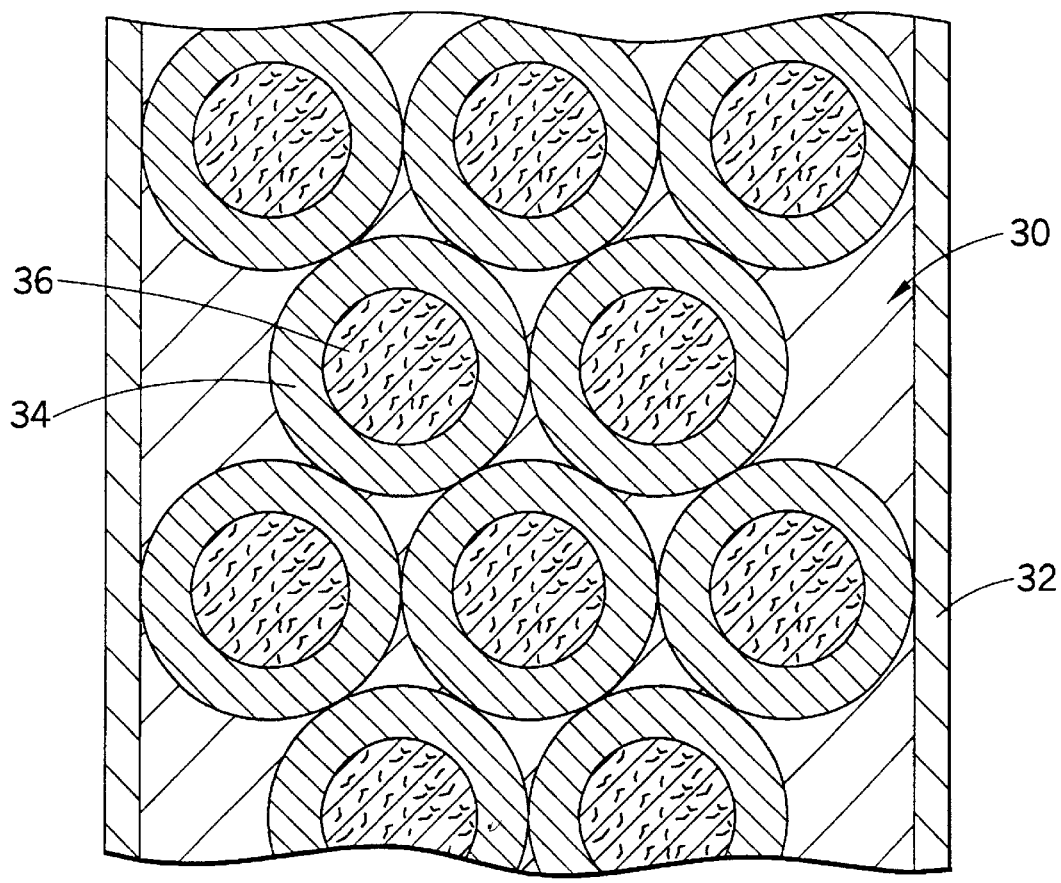
FIG. 19 shows an initially non-densely packed aggregate of closed cells. The open space is filled or infiltrated with a casting metal or polymer.

FIGS. 18A–E show examples of cell and cell aggregate preparation using a metal sheet 10 (e.g., sheet steel) for the cell walls. The sheet metal 10 is shown in FIG. 18A. The steps of forming the sheet metal into a cell configuration 12, filling 14 the sheet metal cell with a cell filler 16, sealing the cell 18, 20 and additional shaping or heat treating 22 are exemplified in FIG. 18B. Additional shaping and heat treating operations may not always be necessary, but may be advantageous in certain situations. FIG. 18C represents a diffusion bonded cell body with open interstices which may be left open or filled by infiltration of liquid metal (e.g., Al, Mg) or a liquid polymer or other substance, if desired. A nearly full density or full density aggregate of cells formed by pressure bonding is shown in FIG. 18D. The pressure bonding normally takes place at elevated temperatures to facilitate bonding between cells. Pressure may be applied along one or more axes. FIG. 18E discloses a nearly full density or full density aggregate of cells formed by uniaxial compression. FIG. 19 shows an initially "open" cell steel-graphite aggregate that is filled or infiltrated with a casting metal or polymer. Cast iron, aluminum or magnesium casting alloys are among the metals that may be infiltrated at 30. A mold wall is shown at 32. Circular cells have iron walls 34 and carbon fillers 36. When cast iron is infiltrated, it is applied below the melting temperature of the steel cells, e.g., at 1400° C.

Cells may be encapsulated by the forming, filling and sealing method of claim 18A–18E. Also, encapsulating may be done by electrolytic deposition of a structural metal onto pellets of the cell filler substance, or by depositing liquid metal onto pellets of the cell filler substance, or by vapor deposition of the metal onto the pellet. In the alternative, non-reactive filler material may be ion implanted into a structural metal.

Closed metal cell composites described herein can serve a variety of purposes, including biomedical and industrial applications.

In the biomedical area, closed metal cell composites provide useful substitutes for both hard and soft tissue. For example, the composites can be used for bone implants, hip prostheses, or dental replacements. These closed metal cell composites offer advantages over conventional prosthesis materials such as monolithic metals or ceramics. For example, the elastic moduli (Young's modulus, shear modulus) of metal cell composites can be made to more closely parallel true biological material (bone, cartilage) than would be possible with conventional prosthesis materials. Also, the elastic properties of metal cell composites can be tailored for specific needs. Stiffness gradients can be made to simulate those of the substituted biological mass or as made by design.

A preferred embodiment of a biomedical application for a closed metal cell comprises metal cell walls of biologically nontoxic materials such as titanium, titanium alloy, stainless steel, cobalt-based stainless alloy, nickel-based stainless alloy, gold, gold-alloy or others. The preferred cell interiors for biomedical applications are comprised of a liquid or deformable or pliable substance, preferably a biologically nontoxic material. Such a cell interior material preferably will not react with or degrade the cell wall material during fabrication or during use. The metal cell bodies can be made to be dense and impermeable to liquid or gas, or they can be made with open porosity so as to allow ingrowth of tissue.

The metal cell composite bodies are also relevant for various industrial applications including brake disks and drums, structural materials for machine or pump housings, and gaskets.

Closed metal cell composites can substitute for gray iron castings in brake disks and drums of automobiles, trucks and railroad cars. They can also substitute for carbon/carbon composites for use in aircraft brakes. An advantage of using the closed metal cells composites for these applications is that they are lighter than conventional cast iron. Also, the cost of the composites is relatively low in comparison to the cost of cast iron, or not significantly higher. There is a large cost advantage over carbon/carbon or over brake disks made form Al-alloy or stainless steel. Parts can be fabricated relatively simply using accepted powder metallurgical methods such as sintering, hot pressing, extrusion, and plastic shaping. The composites are easily machined. There are a number of performance advantages including a higher fracture toughness than gray cast iron; higher heat capacity than the same mass of monolithic cast iron or aluminum or stainless steel disks; higher temperature capability than aluminum-based disks; higher damping capacity than most any other conventional brake disk materials; better tribological performance than aluminum-based or stainless steel based disks because of built-in graphite that is provided to the wear surface as material is worn away; can be made with higher thermal conductivity than cast iron or aluminum alloy or stainless steel, e.g., by infiltrating copper into a non-densified, sintered body of steel/graphite cells.

There are several preferred embodiments of closed metal cell composites for brake disks. These include cell walls of iron or steel and cell interiors of graphite. Another preferred embodiment is a cell wall of copper with a graphite interior. Also preferred are cell walls made from any of the metals Fe, Ni, Co, Cr, Al, or Mg with graphite cell interiors. Finally, another embodiment for brake disks includes cell walls of an oxidation-resistant alloy, such as made from Fe, Ni, Co and Cr and a cell interior of graphite.

Structural materials for machine or pump housings provide another viable avenue for metal cell composites. The composites can substitute for cast metal housings made of gray cast iron, malleable or ductile cast iron, aluminum castings, magnesium castings, bronze castings or titanium castings. They can also substitute for housings made from machined monolithic materials. There are advantages of using metal cell composites in these instances. The composites are lightweight, provide dimensional rigidity and vibration damping for noise reduction. They are relatively low-cost materials, and may be fabricated using accepted powder metallurgical methods. There is a higher fracture toughness per mass than with conventional castings, and the composites are readily machinable. The composites can be used as housings for motors, engines, transmissions, turbines, lathes, milling machines, hand tools, and pumps. Preferred materials for these applications include cell walls of iron or steel, nickel alloys or titanium alloys, all with cell interiors of graphite.

Compacted metal cell composites can be made to serve as gaskets in engines, machines, turbines pumps, pressure vessels and vacuum equipment. They provide low modulus and large elastic strain(resilience) combined with ability for effective vibration or sound damping. Metal cell gaskets can be used for high temperature applications. They can substitute for conventional elevated temperature gaskets, monolithic metal gaskets, metal felt gaskets or nonmetal gaskets.

There are advantages associated metal cell gaskets. For example, there is a larger elastic range than that associated with monolithic materials. Also, metal cell gaskets can be made air or vacuum tight or, if desired, can be made with open porosity. They are manufactured according to accepted powder metallurgical methods. They have plastic formability, yet they retain elastic range or resilience. Finally, they are of relatively low cost.

A preferred embodiment structure for closed cell metal gaskets would include cell wall of most any ductile structural metal, e.g., Fe, Ni, Co, Cr, Al, Cu, Ag, Au, Ti, Zr, Zn, Sn, Pt, Ir, or Pd. Cell interiors are filled with a pliable, elastic, nonreacting substance. Depending upon the cell wall metal and the use temperature range, the cell filling materials will be chosen to satisfy the properties of being pliable, elastic and non-reacting with each other to a degree that no mutual degradation occurs. The cell filling materials will also be chosen to be nonreactive with the cell walls to a degree that no property degradation occurs during fabrication or use.

These gasket cell interiors may be filled with graphite or pitch or with low modulus alkali metals such as Li, Na, K, Rb, Cs, Mg, Ca, Sr, Ba, Al or mixtures thereof or with mixed masses of Li and LiF, or Na and Na Cl, or K and KCL, or Ca and CaCl, or they may be filled entirely with salt, especially with low melting salts so that the cell interiors are either liquid or mushy, i.e., a mixture of solid and liquid, at the use temperatures. Polymers, especially rubbery polymers, with low modulus of elasticity are suitable cell filler materials for gaskets that are used at not too high temperatures, i.e., at temperatures below which thermal degradation of the polymers would occur.

The invention has been described with reference to the preferred embodiment. Obviously modifications and alterations will occur to others upon a reading and understanding of this specification. It is intended to include all such modifications and alterations insofar as they come within the scope of the appended claims or the equivalents thereof.

Having described the invention, the following is claimed:

1. A composite material comprising a plurality of fully closed structural metal cells joined into a random aggregate arrangement, each fully closed structural metal cell encapsulating a filler therein for providing characteristics desired in the material, said filler comprising one or more of a liquid, a powder, a paste or slurry, or a soft or viscous solid.

2. The material of claim 1 wherein the resulting composite material is formed into a structural housing for machines or pumps including metal cell walls containing nickel, iron or titanium, and a graphite filler.

3. The material of claim 1 wherein the closed structural metal cells are joined by sinter or pressure bonding.

4. The material of claim 1 wherein a binder joins the closed cells together.

5. The material of claim 1 wherein the filler is a powder.

6. The material of claim 1 wherein the filler is a liquid.

7. The material of claim 1 wherein the filler is a soft or viscous solid.

8. The material of claim 1 wherein the structural metal cell is comprised of a generally polygonal, square or circular configuration.

9. A biomedical prosthesis material including a plurality of closed biologically nontoxic metal cells joined into a random aggregate arrangement, each cell containing a nontoxic filler.

10. The material of claim 9 wherein the structural metal from which the closed metal cell is formed includes titanium and the filler is graphite powder.

11. The material of claim 9 wherein the structural metal from which the closed metal cell is formed includes titanium and the filler is calcium oxide powder.

12. The material of claim 9 wherein the structural metal from which the closed metal cell is formed includes titanium and the filler includes a calcium phosphate compound such as hydroxy apatite powder.

13. A tribological structure including a plurality of fully closed cells formed from a structural metal having a melting temperature greater than 500° C. and joined into a random aggregate arrangement, each cell containing a non-solid filler having tribological properties, the closed cells joined together in the form of a random aggregate body.

14. The material of claim 13 wherein the resulting composite material forms a brake disk including a plurality of closed cells formed from a structural metal having a melting temperature greater than 500° C., each closed cell containing a non-solid filler having tribological properties for fusion brake systems, the closed cells joined together in the form of an aggregate body configured as a brake disk and being lightweight, strong and having damping characteristics.

15. The brake disk of claim 14 wherein the closed cells are adapted for controlled release of the nonsolid filler from the brake disk for sustained tribological properties.

16. The material of claim 14 wherein the structural metal from which the closed metal cell that is formed includes iron and the filler includes powdered graphite.

17. The material of claim 13 wherein the resulting composite material forms a journal bearing including a plurality of closed cells formed from a structural metal having a melting temperature greater than 500° C., each closed cell containing a non-solid filler having tribological properties for fusion brake systems, the closed cells joined together in the form of an aggregate body configured as a journal bearing.

18. A metal cell gasket including a plurality of fully closed structural metal cells joined into a random aggregate arrangement including metal cell walls of a ductile structural metal and a pliable, elastic, nonreacting filler that is nonreactive with the metal cell.

* * * * *